(12) United States Patent
Meise

(10) Patent No.: US 10,080,880 B2
(45) Date of Patent: Sep. 25, 2018

(54) DEVICE FOR CONNECTING MEDICAL DISPOSABLE ARTICLES IN A STERILE MANNER

(71) Applicant: Heinz Meise GmbH, Schalksmuehle (DE)

(72) Inventor: Heinz Meise, Schalksmuehle (DE)

(73) Assignee: Heinz Meise GmbH, Schalksmuehle (DE)

( * ) Notice: Subject to any disclaimer, the term of this patent is extended or adjusted under 35 U.S.C. 154(b) by 104 days.

(21) Appl. No.: 15/114,928

(22) PCT Filed: Feb. 11, 2015

(86) PCT No.: PCT/EP2015/052855
§ 371 (c)(1),
(2) Date: Jul. 28, 2016

(87) PCT Pub. No.: WO2015/121296
PCT Pub. Date: Aug. 20, 2015

(65) Prior Publication Data
US 2016/0339224 A1 Nov. 24, 2016

(30) Foreign Application Priority Data
Feb. 11, 2014 (DE) .................. 20 2014 100 585 U

(51) Int. Cl.
*A61M 39/10* (2006.01)
*A61M 39/18* (2006.01)
*A61M 39/22* (2006.01)

(52) U.S. Cl.
CPC ............ *A61M 39/10* (2013.01); *A61M 39/18* (2013.01); *A61M 39/221* (2013.01);
(Continued)

(58) Field of Classification Search
CPC ...... A61M 2039/1038; A61M 39/1011; A61M 2039/1072; A61M 2039/1094; A61M 39/221
See application file for complete search history.

(56) References Cited

U.S. PATENT DOCUMENTS 5,492,147 A 2/1996 Challender et al.
6,152,913 A * 11/2000 Feith .................... A61M 39/10
604/533

(Continued)

FOREIGN PATENT DOCUMENTS

DE 20 2009 008 274 U1 9/2009
WO 2006122406 A1 11/2006
(Continued)

OTHER PUBLICATIONS

International Search Report of PCT/EP2015/052855, dated Jul. 17, 2015.

*Primary Examiner* — Nathan R Price
*Assistant Examiner* — Melissa A Snyder
(74) *Attorney, Agent, or Firm* — Collard & Roe, P.C.

(57) ABSTRACT

The invention relates to a device for sterile connection of single-use medical articles, consisting of an outlet connector (1), which has an outlet cylinder (4) that is equipped with a seal (6) and that is closed at one of its ends. A union nut (8) is provided on the outlet connector (1), and of an inlet connector (2), which can be connected with the outlet connector (1) and which is closed at one of its ends. The outlet connector (1) and the inlet connector (2) are respectively closed at their ends turned toward one another with a perforation seal (9, 9').

6 Claims, 15 Drawing Sheets

(52) U.S. Cl.
CPC ............... *A61M 2039/1033* (2013.01); *A61M 2039/1038* (2013.01); *A61M 2039/1066* (2013.01); *A61M 2039/1094* (2013.01)

(56) References Cited

U.S. PATENT DOCUMENTS

| | | |
|---|---|---|
| 2003/0060804 A1 | 3/2003 | Vaillancourt |
| 2008/0004600 A1 | 1/2008 | Kitani et al. |
| 2008/0264450 A1* | 10/2008 | Baldwin ............... A61M 39/26 134/22.1 |
| 2009/0099552 A1* | 4/2009 | Levy ..................... A61M 39/10 604/533 |
| 2011/0074148 A1 | 3/2011 | Imai |
| 2011/0240158 A1 | 10/2011 | Py |

FOREIGN PATENT DOCUMENTS

| | | |
|---|---|---|
| WO | 2008070220 A1 | 6/2008 |
| WO | 2008/094707 A1 | 8/2008 |

* cited by examiner

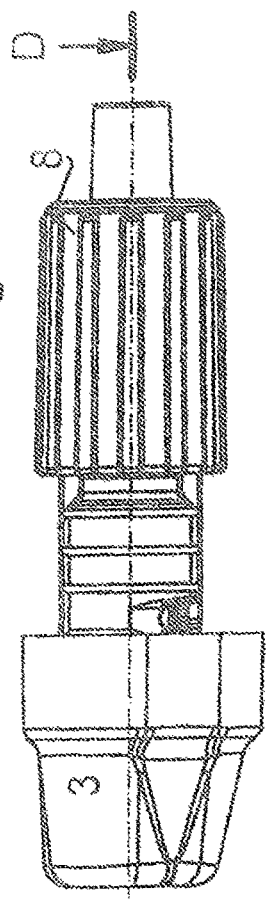
Fig. 1
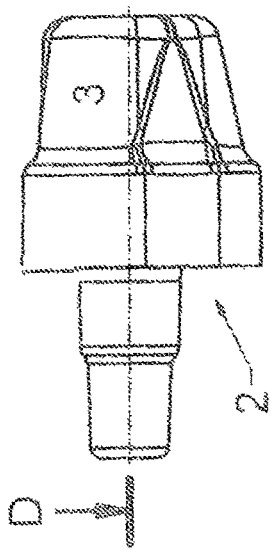
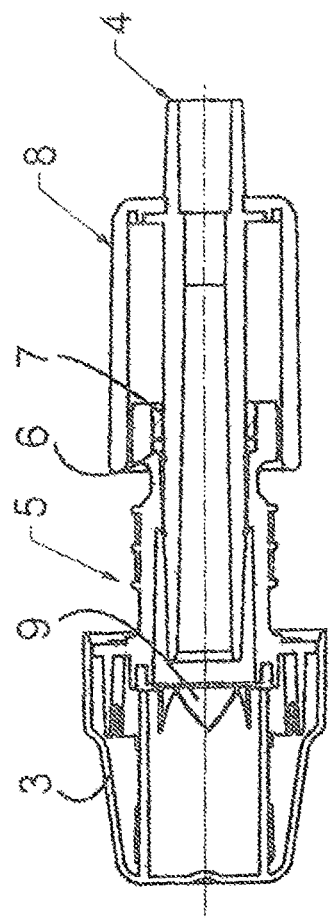
Fig. 2
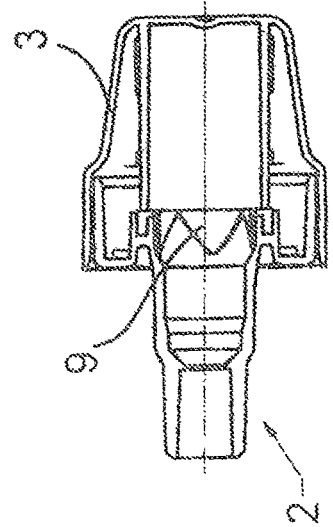

Fig. 7
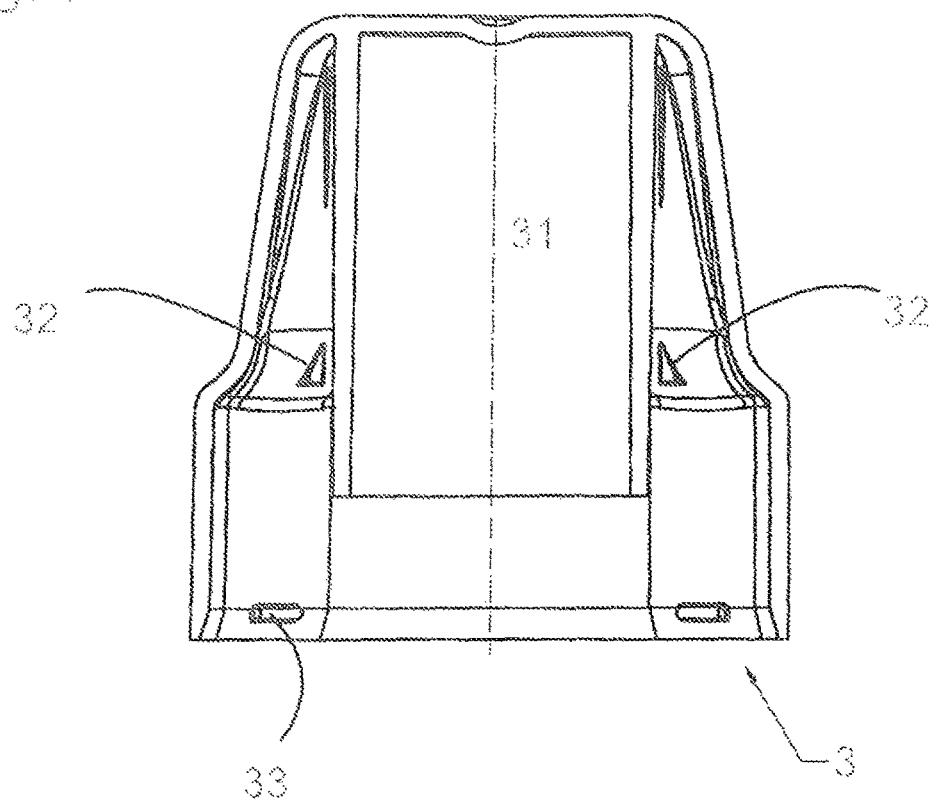
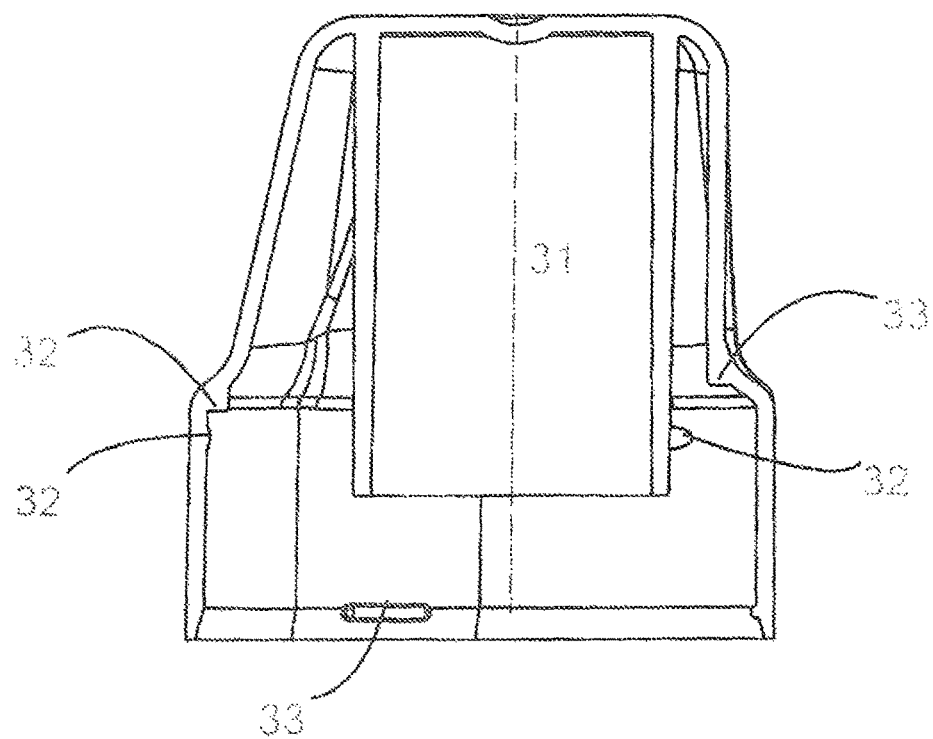

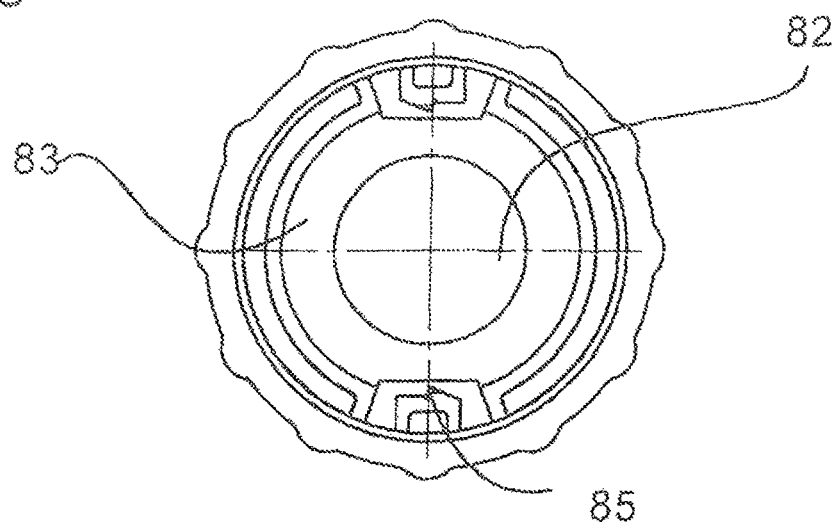
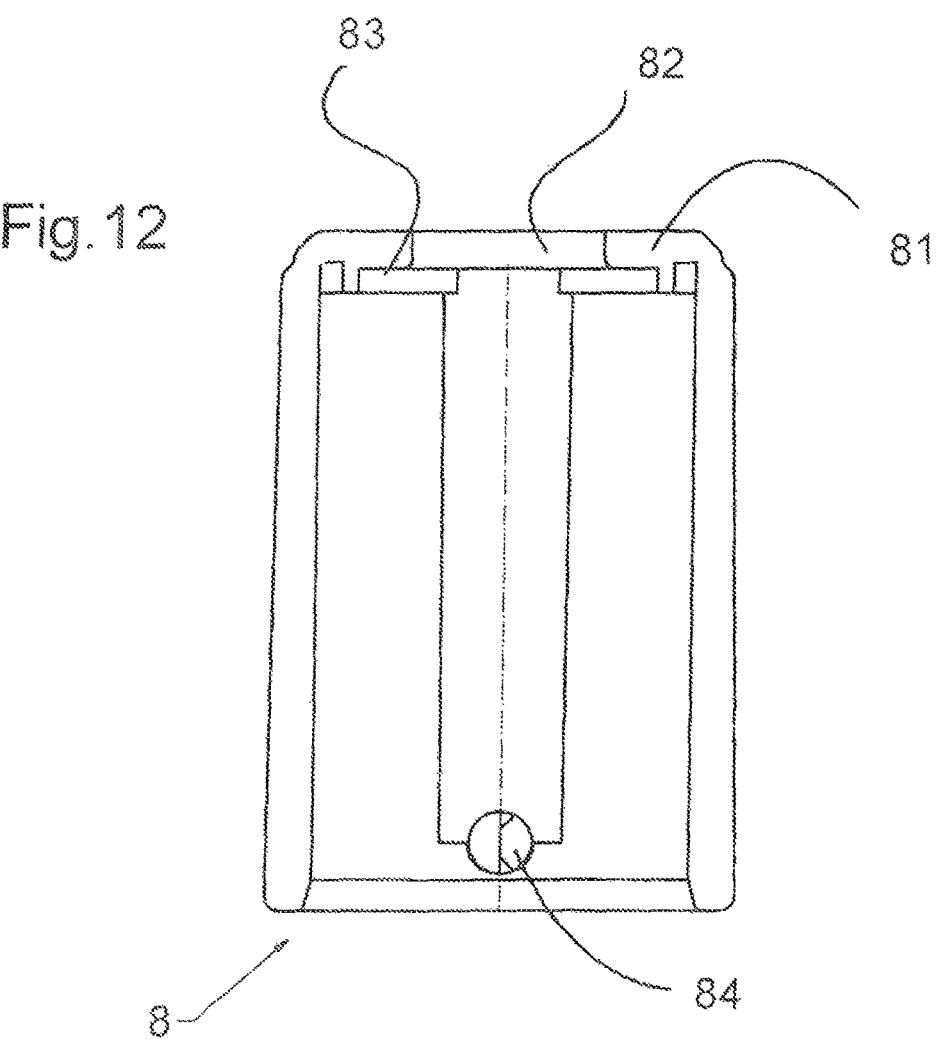

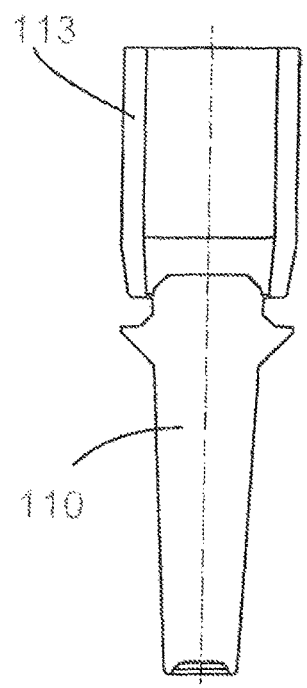

DEVICE FOR CONNECTING MEDICAL DISPOSABLE ARTICLES IN A STERILE MANNER

CROSS REFERENCE TO RELATED APPLICATIONS

This application is the National Stage of PCT/EP2015/052855 filed on Feb. 11, 2015, which claims priority under 35 U.S.C. § 119 of German Application No. 20 2014 100 585.4 filed on Feb. 11, 2014, the disclosure of which is incorporated by reference. The international application under PCT article 21(2) was not published in English.

The invention relates to a device for sterile connection of single-use medical articles, consisting of an outlet connector, which has a tubular piece that is equipped with a seal and adjacent thereto with exit windows and is closed at one of its ends with a closure, and of an inlet connector, which has a holder in which a guide element is disposed.

Devices of the type considered here find uses in diverse ways in the medical field, for example in the area of blood donors, blood transfusions, dialysis and the like for connection of flexible tubes, centrifuge bells, etc. Besides a reliable connection of the respective single-use article, an important criterion of such devices consists in the sterility of the connection. In each case the device must ensure that no bacteria or extraneous substances penetrate into the connection during connection of the single-use articles and then potentially be transported with the liquid into the body of the respective patient and may cause infections there.

For provision of a sterile connection, usually a sterilization process is carried out on the devices to be connected. This may be achieved in various ways, for example by means of superheated steam in an autoclave. The use of sterile-packaged ends, which are unpacked and connected directly only just before use, is also known. However, the known solutions are on the one hand expensive and on the other hand do not guarantee any completely sterile connection.

For avoidance of the sterilization process for the parts to be connected, a device for sterile connection of single-use medical articles, in which the tubular piece with its exit windows is disposed movably in the guide element, is known from DE 20 2009 008 274 U1. Passage openings are formed in the guide element. Furthermore, a sleeve on which a union nut is provided is disposed displaceably on the tubular piece. The known device fulfills the requirements imposed on it with respect to the sterility of the connection. Nevertheless, it has been shown that, during the flow of blood, for example, through the known device, slight impairment of the blood can occur. For example, impairment of the outer skin of the red blood cells has been observed, occurring during the exit of the blood from the passage openings. Because of these impairments, hemoglobin may be released, which reduces the quality of the blood.

The invention intends to provide a remedy here. The task of the invention is to create a device for sterile connection of single-use medical articles that on the one hand permits the required sterility during connection and on the other hand avoids impairment of the media flowing through the device. This task is accomplished by the device according to the invention.

With the invention, a device for sterile connection of single-use medical articles is created that on the one hand permits the required sterility during connection and on the other hand avoids impairment of the media flowing through the device. At the same time, the handling is simple.

Other improvements and configurations of the invention are specified in the other dependent claims. Exemplary embodiments of the invention are illustrated in the drawing and will be described in detail hereinafter. Therein:

FIG. 1 shows the elevation view of an inlet and outlet connector with protective caps;

FIG. 2 shows the section along the line D-D in FIG. 1;

FIG. 7 shows the section through a protective cap;

FIG. 12 shows the section through a union nut;

FIG. 13 shows the side view from the left of the union nut illustrated in FIG. 12;

FIG. 23 shows the section through a breakaway part with a sleeve.

Figure 3:
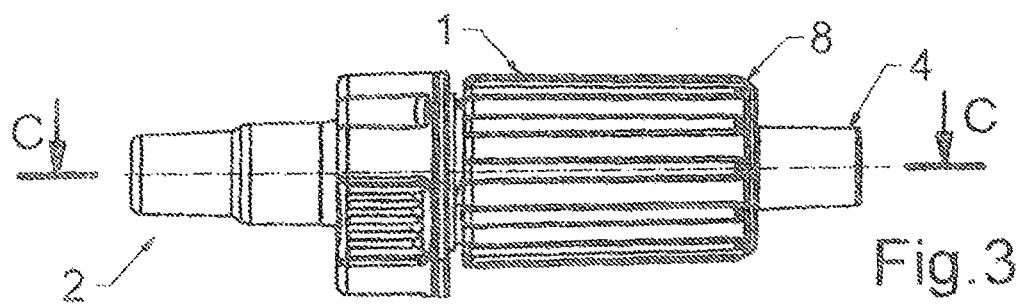
FIG. 3 shows the view of the device in the condition of inlet and outlet connectors connected with one another.
Figure 4:
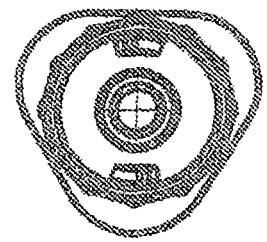
FIG. 4 shows the side view from the right of the device illustrated in FIG. 3.
Figure 5:
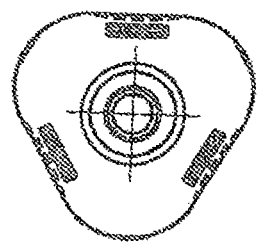
FIG. 5 shows the side view from the left of the device illustrated in FIG. 3.

The device chosen as exemplary embodiment for sterile connection of single-use medical articles consists of an outlet connector 1 and an inlet connector 2, which engage displaceably one in the other. Before their connection, outlet connector 1 and inlet connector 2 are respectively closed by a closure cap 3.

Outlet connector 1 has an outlet cylinder 4, which is rotationally symmetrically shaped. Outlet cylinder 4 is provided at one of its ends, turned away from the inlet connector 2, with a conically formed tube seat 41, which serves for connection with the respective tube. A stop 42, which is formed in dish-like manner and to which a cylindrical portion 43 is attached, is attached, to tube seat 41. Snap-in points 44, beyond which the outlet cylinder 4 tapers conically at its free end, are provided on portion 43. The end is formed by a sealing lip 45.

Furthermore, the outlet connector 1 comprises an outlet, torso 5, in which the outlet cylinder 4 is disposed displaceably. One of its ends is formed by a ring 51, on which a portion 52 of smaller diameter is attached. The inside diameter of the portion 52 corresponds with the outside diameter of the portion 43 of the outlet cylinder 4. The portion 52 is bounded internally by a snap-in nose 53, which in the assembled condition cooperates with the snap-in points 44 of the outlet cylinder 4. The outlet cylinder 4 is provided externally with three ribs 54 in the exemplary embodiment.

The end of the outlet torso 5 turned away from the ring 51 is formed by a coupling part 55. The coupling part 55 consists of a flange 56, on which a overhanging structure 57 is molded that is oriented parallel to the longitudinal centerline of the outlet torso 5 and that overhangs the front end of the outlet torso 5. The overhanging structure 57 has a substantially triangular contour. The free end of the overhanging structure 57 has a snap-in nose 58. A sawtooth-shaped interlocking device 59 is disposed between the ribs 54 and the flange 56. An annular slot 10 is machined into the front end of the outlet torso 5.

In assembled condition, a seal 6 in the form of an O-ring is disposed between outlet cylinder 4 and outlet torso 5. The seal 6 rests on the one hand on the cylindrical portion 43 of the outlet cylinder 4, on the other hand the seal 6 bears against the foot of the ring 51 of the outlet cylinder 5. The seal 6 is secured by a snap ring 7.

A rotationally symmetrically shaped union nut 8 is provided on the outlet connector 1. In the exemplary embodiment it is made in one piece. The union nut 8 is provided externally with a knurling, which leads to art improvement during handling. At its end, the union nut 8 is closed with a cover 81, which has at its center an opening 82, which in the assembled condition serves for passage of the outlet cylinder 4. A recess 83, in which the stop 42 of the outlet cylinder 4 is braced in assembled condition, is formed internally around the opening 82. The union nut 8 is openly configured on the end turned away from the cover 81. In the front region it is provided with a toothing 84, which corresponds with the interlocking device 59 of the outlet torso 5. Two diametrically opposite guide knobs 85, which in the end position of the union nut 8 snap into the interlocking device 59 of the outlet torso 5, are adjacent to the toothing 84 in the inside of the union nut 8.

At its end turned toward the inlet connector 2, the outlet connector 1 is closed with a perforation seal 9, which consists of an elastomer or silicone. It has a ring-like base body 91, which in assembled condition is positioned in the annular slot 10 in the outlet cylinder 5. A perforation element 92 is molded onto the base body 91. In a modification of the exemplary embodiment, the perforation element 92 may also be incorporated in the base body 91 by the 2-component injection-molding process.

At one of its ends turned away from the outlet connector 1, the inlet connector 2 is provided with a conically shaped tube seat 21, which serves for connection with the respective tube. The inlet connector 2 has a through-bore 22, which in its middle region is multi-stepped. Thereby a sealing cone 23 is established, on which the sealing lip 45 of the outlet connector 4 bears in opened condition of the device.

At its end turned away front the tube seat 21, a coupling part 25 is disposed on the front end. The coupling part 25 consists of a overhanging structure 26, which is oriented parallel to the longitudinal centerline of the inlet connector 2 and which overhangs the front end of the inlet connector 2. The overhanging structure 26 has a substantially triangular contour. The inside width of the overhanging structure 26 corresponds substantially to the outer dimensions of the overhanging structure 57 of the coupling part 55, and so the overhanging structure 57 travels into the overhanging structure 26 during the assembly of the device. An annular slot 10' is machined into the front end of the inlet connector 2.

At its end turned toward the outlet connector 1, the inlet connector 2 is closed with a perforation seal 9', which also consists of an elastomer or silicone. It has a ring-like base body 91', which in assembled condition is positioned in the annular slot 10' in the inlet connector 2. A perforation element 92', which extends into the bore 22 of the inlet connector 2, is molded onto the base body 91'.

In the non-connected condition of the device (FIG. 2), the outlet connector 1 and the inlet connector 2 are respectively closed with the closure cap 3. In the frontal view, the closure cap 3 has a substantially triangular contour, which corresponds with the shape of the overhanging structures 26 and 57. The protective cap 3 is provided internally with a guide cylinder 31, the diameter of which corresponds to the diameter of the front ends, turned toward one another, of the inlet connector 2 as well as of the outlet torso 5. Projections 32 are disposed externally on the guide cylinder 31, in a manner distributed over its circumference. In the region of its open end, the protective cap 3 has three snap-in arches 33.

In closed condition, the guide cylinder 31 is braced directly next to the annular slots 24 and 56 on the front ends of the inlet connector 2 as well as of the outlet torso 5, without also coming into contact with the perforation seals 9, 9'. At the same time, the overhanging structures 26 and 57 bear on the project ions 32. The snap-in arches 33 in this condition engage behind the coupling part 25 or the flange 56, whereby a reliable arrangement is ensured.

Figure 6:
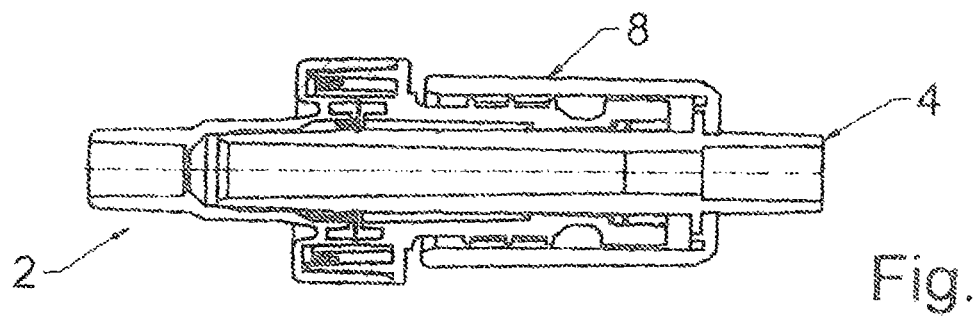
FIG. 6 shows the section along the line C-C in FIG. 3.
Figure 8:
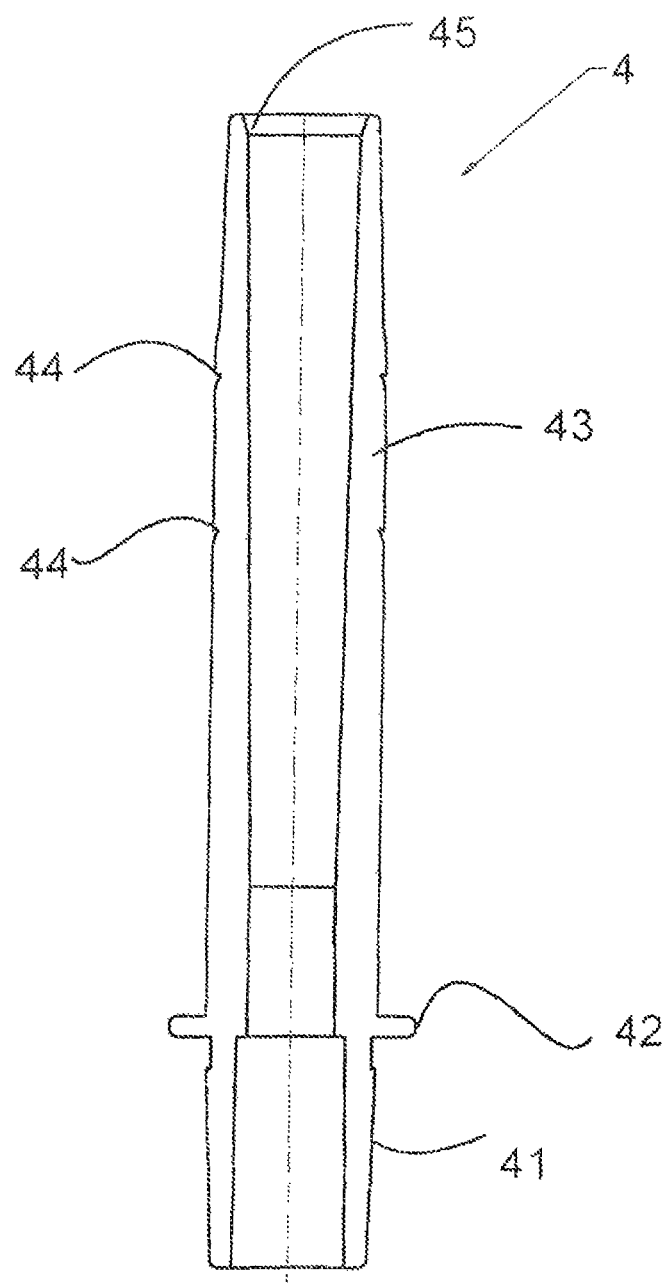
FIG. 8 shows the section through an outlet cylinder.
Figure 9:
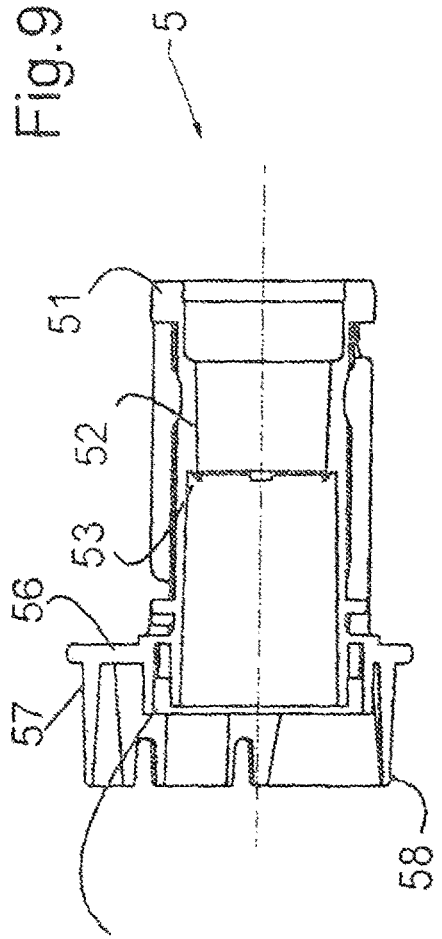
FIG. 9 shows the section through an outlet torso.
Figure 11:
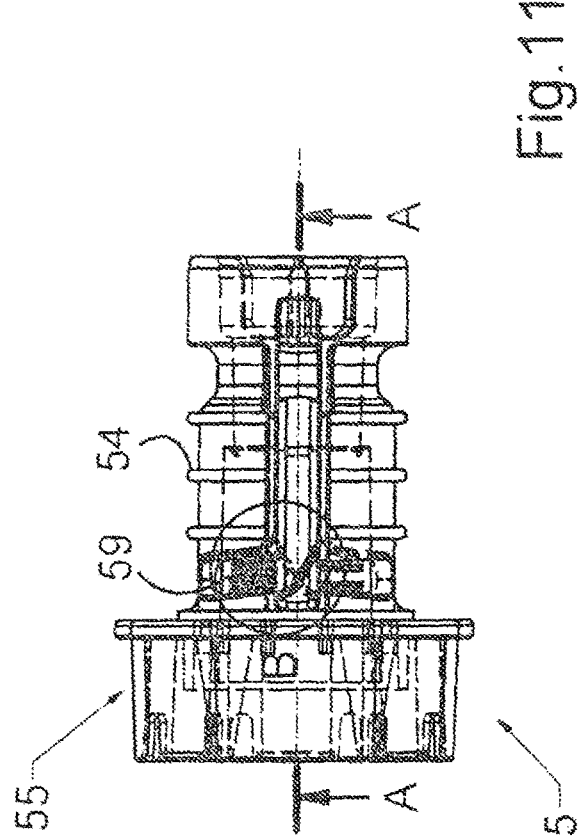
FIG. 11 shows the view of the outlet torso illustrated in FIG. 9.
Figure 10:
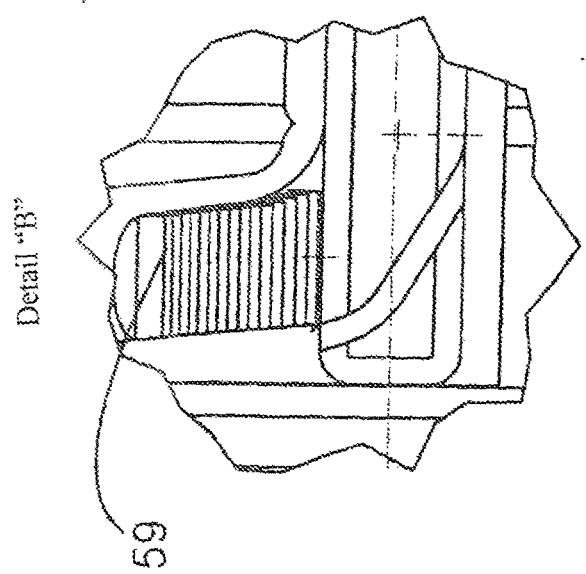
FIG. 10 shows the side view from the left of the outlet torso illustrated in FIG. 9.
Figure 14:
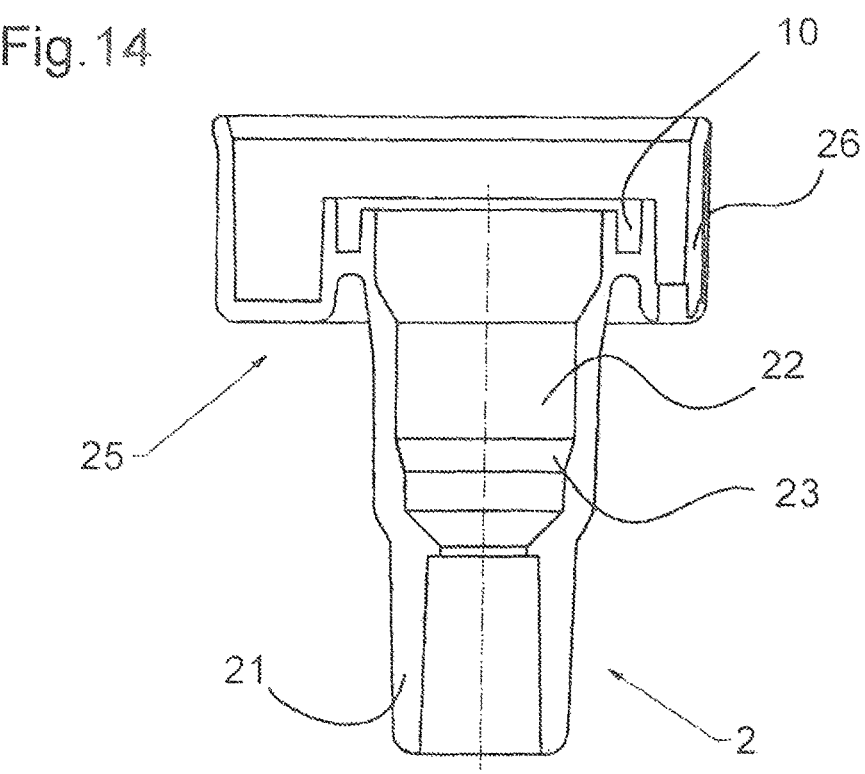
FIG. 14 shows the section through an inlet connector.
Figure 15:
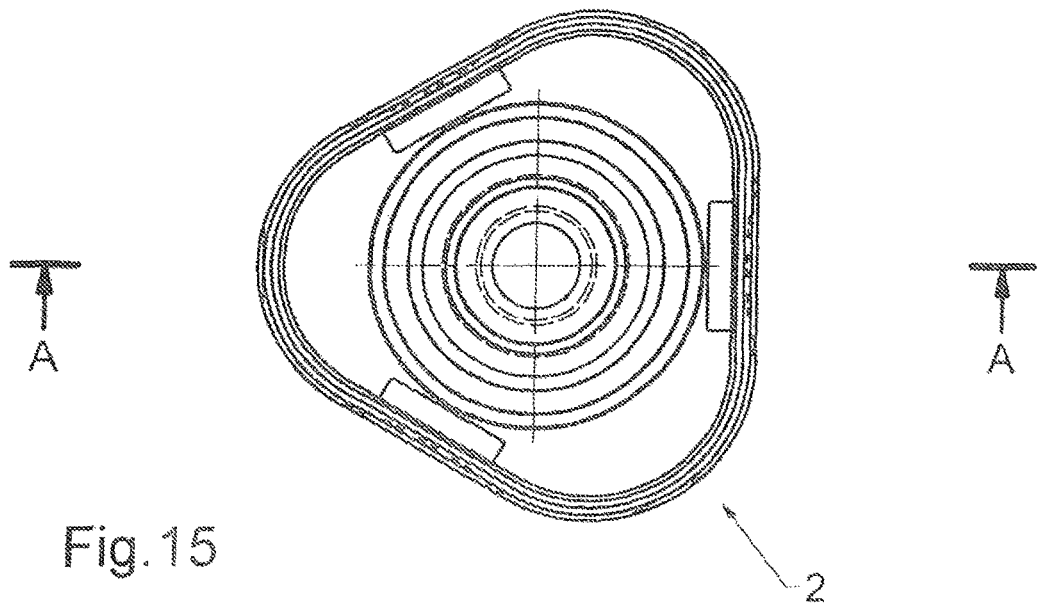
FIG. 15 shows the side view from the right of the inlet connector illustrated in FIG. 14.
Figure 16:
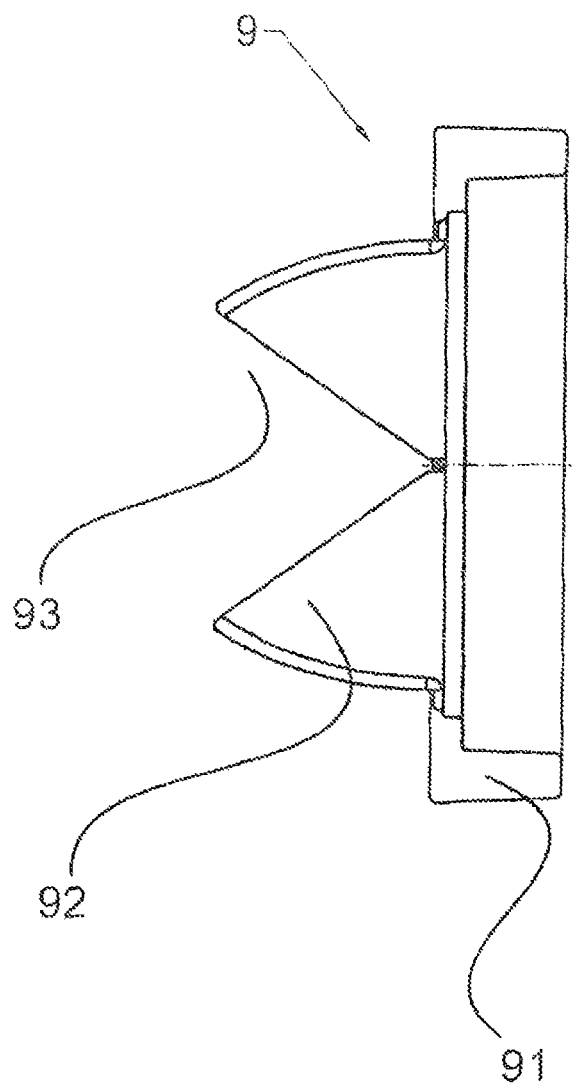
FIG. 16 shows the section through a perforation seal.
Figure 17:
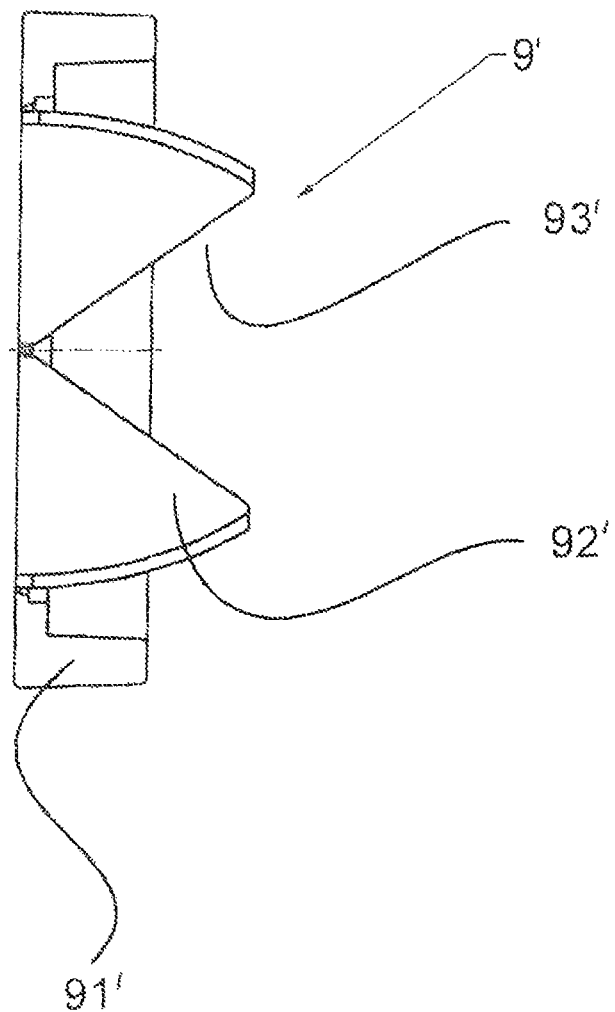
FIG. 17 shows the section through a perforation seal in another configuration.
Figure 18:
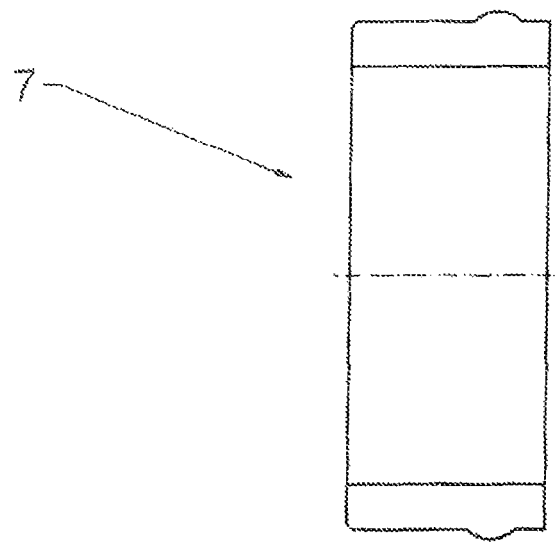
FIG. 18 shows the section through a snap ring.
Figure 19:
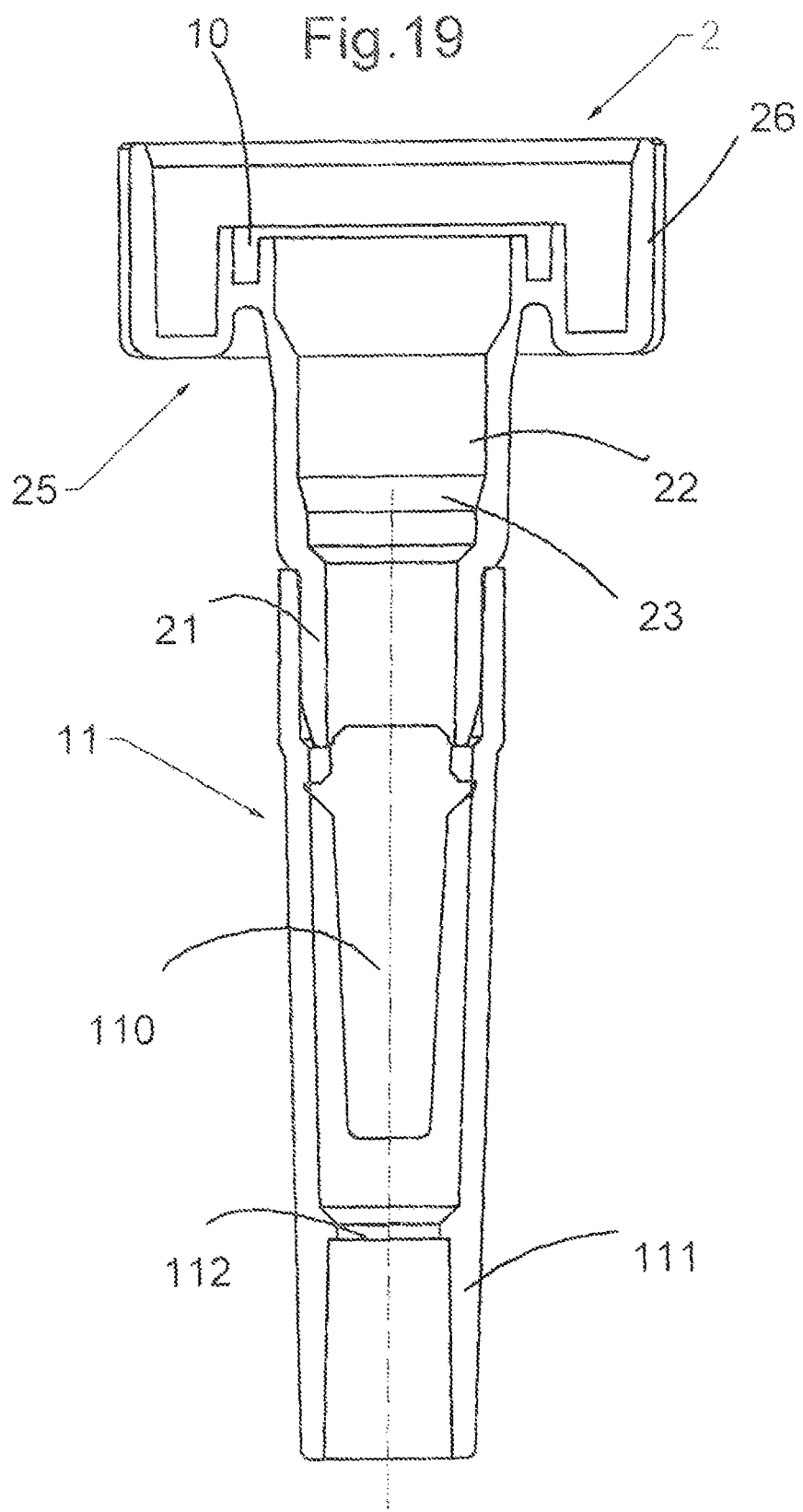
FIG. 19 shows the section through an inlet connector with breakaway connector and breakaway part.
Figure 20:
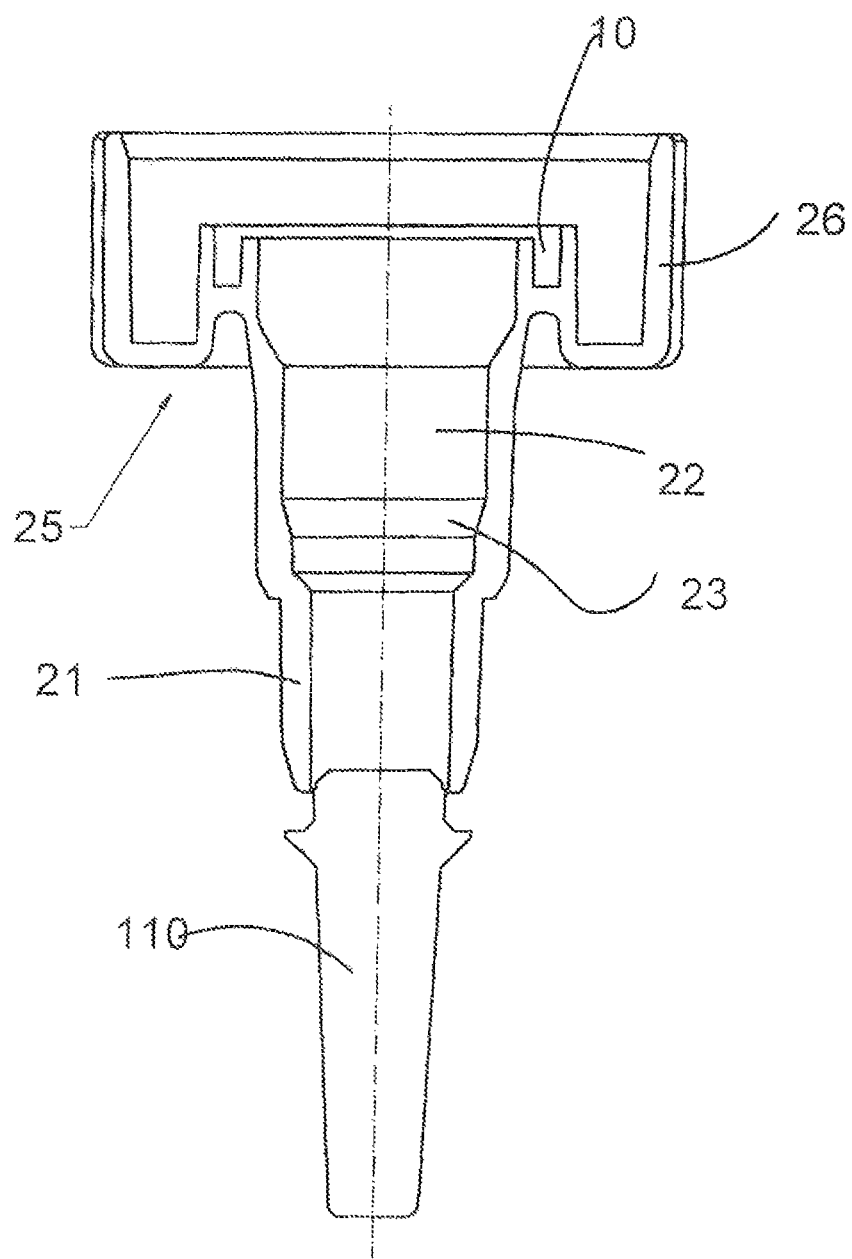
FIG. 20 shows the section through an inlet connector with breakaway part without breakaway connector.

For connection of outlet connector 1 and inlet connector 2, the closure caps 3 are first removed. Then the outlet connector 1 and the inlet connector 2 are brought toward one another, in the process, the overhanging structure 26 and the overhanging structure 57 travel into one another. In their end position, the connectors 1 and 2 latch together by means of the snap-in noses 53 on the outlet torso 5. In this position, the front ends of the outlet connector 1 and of the inlet connector 2 perceptibly butt against one another in gap-free manner (FIG. 6). At the same time, the perforation seals 9 and 9' lie one above the other in coinciding manner. In this condition, the connectors 1 and 2 are still sealed against one another, and so no medium can yet pass from one into the other connector.

To release the flow, the union nut 8 is moved toward the inlet connector 2. Because of the stop 42 of the outlet cylinder 4 braced in the recess 83 of the union nut 8, this displacement of the union nut 8 simultaneously leads to an axial movement of the outlet cylinder 4 toward the inlet connector 2. This movement is executed until the toothing 84 of the union nut 8 comes into contact with the interlocking device 59. Since this has a helical contour, a rotation of the union nut 8 simultaneously leads to a further axial movement of the union nut 8 as well as of the outlet cylinder 4 toward the inlet connector 2. During its axial movement, the sealing lip 45 punches through the perforation seals 9 and 9', whereby the perforation seals 9, 9' tear open and a V-shaped notch 93, 93' is respectively produced. Flow through the device is then enabled. The end position is reached when the union nut 8 bears on the flange 56. Likewise the sealing lip 45 then bears on the sealing cone 23 of the inlet connector 2. The flow of the respective medium is thus possible, while the connectors 1 and 2 are reliably sealed against one another. Furthermore, any accidental loosening of the connectors 1 and 2 is prevented by virtue of the sawtooth-like shape of the toothing 84, which effectively prevents reverse rotation of the union nut 8 and thus opening of the connection.

As a supplement to the device described in the forgoing, the possibility exists of providing a breakaway connector 11 on the inlet connector 2, as illustrated in the exemplary embodiment according to FIGS. 19 to 23. In this embodiment according to FIGS. 19 and 20, in principle the inlet connector 2 finds use in its form described hereinabove. However, a breakaway part 110 in the form of a plunger, which is connected with, the front end of the tube seat 21 via a kind of film hinge (FIG. 20), is additionally molded onto the tube seat 21. In this condition, the bore 22 is closed by the breakaway part 110. A tube adapter 111, which consists of flexible material, is additionally pushed, onto and adhesively bonded to the tube seat 21. The tube adapter 111 surrounds the breakaway part 110 completely. Spaced apart from the free end of the breakaway part 110, a cross-sectional constriction 112 is formed in the tube adapter 111.

Figure 21:
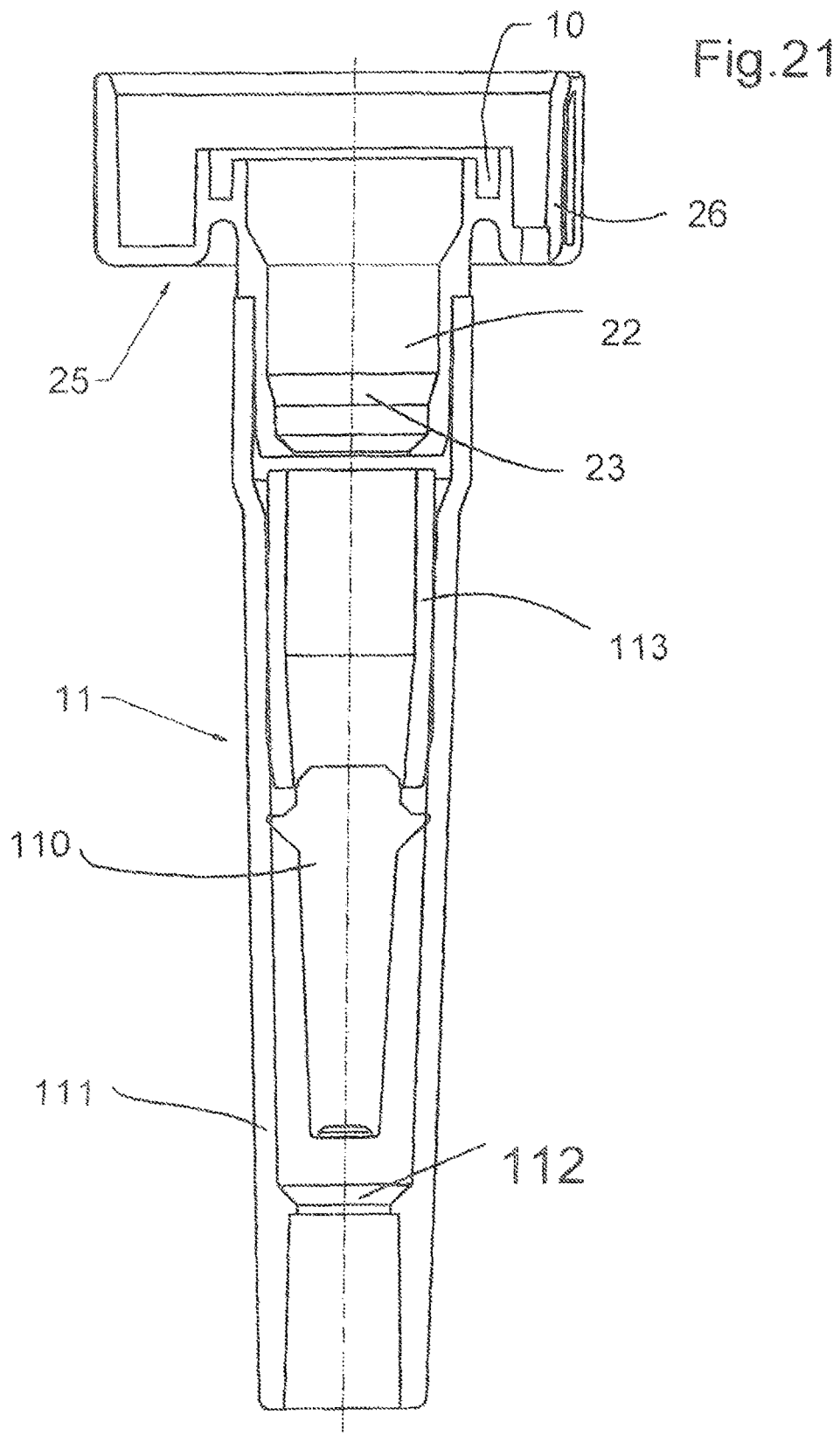
FIG. 21 shows the section through an inlet connector with breakaway connector and breakaway part in another configuration.
Figure 22:
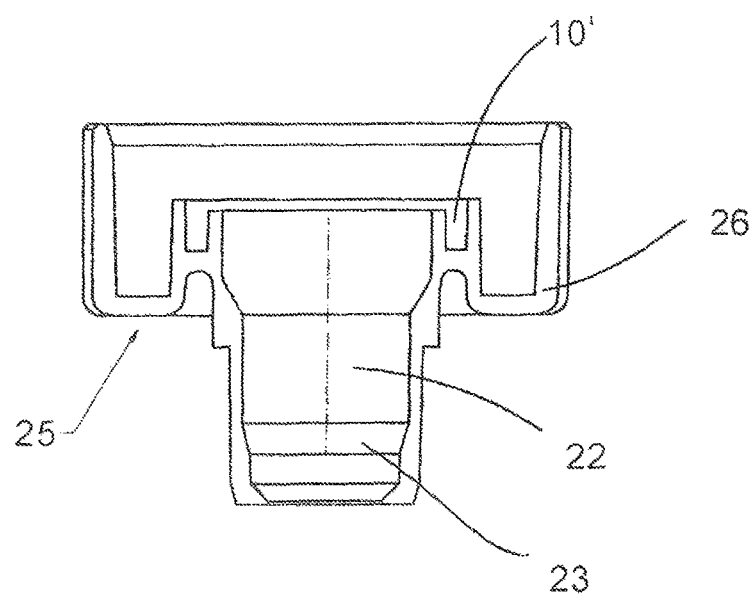
FIG. 22 shows the section through the inlet connector illustrated in FIG. 21.

In the exemplary embodiment according to FIGS. 21 to 23, the inlet connector 2 is modified to the effect that the tube seat 21 is omitted. Instead, the tube adapter 111 is pushed onto and adhesively bonded to the wall surrounding the bore 22. The tube adapter 111 also has the cross-sectional constriction 112. The breakaway connector 11 also comprises the breakaway part 110 in this embodiment. However, it is molded not onto the inlet connector 2 but instead onto a sleeve 113, which together with the breakaway part 110 is surrounded by the tube adapter 111.

The device according to the invention provides a capability for a sterile connection of single-use medical articles. This is ensured by the fact that, in non-connected condition of the respective single-use medical article, on the one hand the outlet connector 1 is closed by the perforation seal 9 at its end turned away from the tube. As a consequence of this, the internal region of the outlet cylinder 4 provided for the flow of the respective liquid is sealed against the environment. This is true even after removal of the closure caps 3. Furthermore, accidental impairment of the seal 9 is prevented by the protective cap 3.

Likewise the sealing in the case of the inlet connector 2 is achieved by means of the perforation seal 9', which seals the bore 22 of the inlet connector 2 provided for the flow of the liquid against the environment, and in fact does so even after removal of the protective cap 3. Accidental impairment of the seal 9' is also prevented by the protective cap 3.

The flow through the device is released only by the displacement of the outlet cylinder 4 toward inlet connector 2 and the entry of the sealing lip 45 into the connector 2 and perforation of the seals 9 and 9'. However, since in this condition the coupling parts 25 and 55 have already traveled into one another, any contact with the environment is also excluded in this respect. Consequently, a sterile connection is established by the positioning of the seals 9, 9' in the bore 22 of the connector 2. Because of the set-back, arrangement of the seals 9 and 9', any accidental contamination after removal of the protective caps 3 is prevented. Furthermore, because of the various snap connections, simple assembly as well as a high stability of the connection is established.

Furthermore, in the exemplary embodiments according to FIGS. 19 to 23, the flow is released only when the breakaway connector 11 is actuated. This is achieved by simple kneading or bending of the tube adapter 111 in the region of the breakaway part 110 turned toward the inlet connector 2. Hereby the connection between breakaway part 110 and tube seat 21 or sleeve 113 is separated, so that the flow through the device is released.

The device according to the invention additionally ensures a flow in which the medium can flow through the device in unimpaired manner. This is a consequence of the provision of a smooth tubular flow region without sharp edges. In particular, as soon as the medium from the tube passes into the inlet connector 2, it enters, downstream from the stepped portion in the region of the sealing cone 23, the outlet cylinder 4, which is smoothly formed internally, and from which the medium passes into the tube attached to the outlet connector 1.

Furthermore, the substantially triangular contour of the coupling parts 25 and 55 ensures error-free operation of the device. The same is true for the likewise triangular configuration of the protective caps 3. On the whole, the handling of the device is very simple and operator's errors are avoided.

The invention claimed is:

1. Device for sterile connection of single-use medical articles, comprising
an outlet connector (1), which has an outlet cylinder (4) that is equipped with a seal (6) and which is closed at one of its ends, wherein a union nut (8) is provided on the outlet connector (1), and
an inlet connector (2), which can be connected with the outlet connector (1) and which is closed at one of its ends,
wherein the outlet connector (1) and the inlet connector (2) are respectively closed at their ends turned toward one another with a perforation seal (9, 9'),
wherein the outlet connector (1) comprises an outlet torso (5) with a coupling part (55), which cooperates with a coupling part (25) of the inlet connector (2),
wherein the coupling parts (25) and (55) have a substantially triangular contour, which ensures an error-free operation of the device, and the union nut (8) is provided with a sawtooth-like toothing (84), which corresponds with an interlocking device (59) of the outlet torso (5),
wherein guide knobs (85), which in the end position of the union nut (8) snap into the interlocking device (59) of the outlet torso (5), which prevent reverse rotation of the union nut (8), are disposed internally in the union nut (8), and the interlocking device (59) has a helical contour.

2. Device according to claim 1, wherein the perforation seals (9, 9') have a base body (91, 91'), which in mounted condition is positioned in an annular slot (10, 10') in the inlet connector (2) and/or outlet cylinder (5).

3. Device according to claim 1, wherein the perforation seals (9, 9') comprise an elastomer or silicone.

4. Device according to claim 1, wherein the perforation seals (9, 9') have a perforation element (92, 92').

5. Device according to claim 1, wherein the outlet connector (1) and the inlet connector (2) latch together in their end position and the perforation seals (9, 9') lie one above the other in coinciding manner.

6. Device according to claim 1, wherein a breakaway connector (11) is provided on the inlet connector (2).

* * * * *